United States Patent [19]

Hawks

[11] Patent Number: 4,712,536

[45] Date of Patent: Dec. 15, 1987

[54] RECTAL SPECULUM WITH OBTURATOR

[76] Inventor: Robert A. Hawks, 3602 W. Danbury Dr., Glendale, Ariz. 85308

[21] Appl. No.: 4,600

[22] Filed: Jan. 20, 1987

[51] Int. Cl.$^4$ ............................................. A61B 1/12
[52] U.S. Cl. ..................................... 128/3; 128/750
[58] Field of Search ................... 128/3, 4, 5, 6, 7, 8, 128/750; 604/28, 186

[56] References Cited

U.S. PATENT DOCUMENTS

| D. 228,204 | 8/1973 | Hines | D16/14 |
|---|---|---|---|
| 1,596,847 | 8/1926 | Mallory | 128/4 X |
| 2,826,197 | 3/1958 | Leonard | 604/186 |
| 3,132,645 | 5/1964 | Gasper | 128/3 |
| 3,771,522 | 11/1973 | Waysilk et al. | 604/28 |
| 4,190,059 | 2/1980 | Holt | 128/750 |

Primary Examiner—William H. Grieb
Attorney, Agent, or Firm—Herbert E. Haynes, Jr.

[57] ABSTRACT

A rectal speculum assembly for use with a colonic lavage machine includes a speculum and an obturator. The speculum includes an unobstructed main tube for directing fluids into and out of a patient's rectum, and an inlet tube for injecting treatment fluid into the main tube. The inlet tube intersects the main tube, forming an obtuse angle with respect to the proximal end of the main tube, so that inlet fluids are initially directed away from the patient's rectum, and thus do not interfere with fluided waste matter being discharged therefrom. In addition, a thumb rest is provided on the main body of the speculum for holding the speculum steady while the obturator is removed and a waste removal hose is connected.

20 Claims, 5 Drawing Figures

RECTAL SPECULUM WITH OBTURATOR

BACKGROUND OF THE INVENTION

1. Field of the Invention

This invention relates generally to rectal specula, and more particularly, to a speculum for use with a colonic lavage machine.

2. Description of the Prior Art

Devices are known for lavaging the lower intestinal tract of patients suffering from colitis and other similar ailments. Examples of such devices can be found in U.S. Pat. No. 2,826,197 to Leonard, U.S. Pat. No. 3,771,522 to Waysilk et al, and U.S. Pat. No. 4,190,059 to Holt. These devices commonly employ a speculum for directing treating fluids into patient's colon and subsequently allowing the discharge of fluidized waste matter.

Typically, the rectal specula used with the above devices comprise a pair of concentric tubes, including an inlet tube which carries water into the patient's rectum and colon, and a discharge tube which allows fluidized waste matter to flow out of the patient's body. In addition, in order to faciliate insertion of the speculum in the patient's rectal canal, and to decrease the patient's discomfort and possible pain as well as to avoid possible damage to the patient's intestinal tract, the speculum is usually used in combination with an obturator. Typically, an obturator comprises an elongated rod provided with a tapered, round exterior portion at one end, and a handle portion at the opposite end. Normally, the obturator is inserted from the proximal end of the speculum through the hollow interior to extend through the distal end thereof in order to facilitate insertion of the speculum into the patient's rectum, and is then removed from the speculum by use of the handle.

The conventional specula as described above suffer from a number of drawbacks. One problem is that the concentric tube structure makes the specula difficult and expensive to manufacture, as well as inconvenient to clean and maintain. A second problem is that the process of removing the obturator and attaching a discharge hose or conduit to the outlet end of the speculum can be painful to the patient since the inlet end of the speculum is free to rock or slip in the patient's rectum while the hose is being attached.

In an attempt to solve the first of these problems, one speculum has been introduced which does away with the conventional concentric tube structure. This speculum is shown in U.S. Pat. No. Des. 228,204 to Holt. The Holt speculum comprises a pair of intersecting tubes including an unobstructed main tube having a distal end adapted for insertion in a patient's rectum and a proximal or discharge end adapted for connection to a waste removal hose, and an inlet tube connectible to a source of water for permitting injection of water into the main tube. The inlet tube is considerably smaller in diameter than the main tube and is disposed at an acute angle to the discharge end of the main tube. This angle causes a slight inlet current in the direction of the patient's colon when the lavaging machine is in operation.

Once the Holt speculum has been inserted into the patient's body, with an inlet hose having been previously connected to the inlet tube of the speculum, a waste removal hose must be subsequently connected to the proximal end of the main tube due to the need for removing the obturator. Water or other treating fluid from an external source is then allowed to travel through the inlet hose and inlet tube and fills up the main tube and waste removal hose until a sufficient back pressure has been built up to direct the fluid into the patient's lower intestine. Once the fluid pressure in the intestine is equal to or greater than the pressure in the main tube and the waste discharge tube, the water and fluidized waste matter in the intestine is discharged through the speculum. The problem with the Holt structure, however, is that because of the orientation of inlet tube relative to the main tube of the speculum, the discharged waste matter must flow counter to the direction of the inlet current. This means that the pressure on the patient's intestine is relieved much more slowly and less effectively than in a speculum in which the discharge material does not have to fight a counter current. As a result, the patient suffers greater pain and discomfort than is necessary.

Therefore, a need exists for a new and improved rectal speculum which overcomes some of the problems and shortcomings of the prior art.

SUMMARY OF THE INVENTION

In accordance with the present invention, a new and improved rectal speculum is disclosed. The speculum comprises a pair of intersecting tubes including an unobstructed main tube having a distal end adapted for insertion in a patient's rectum and a proximal end for connection to a waste removal hose, and an inlet tube connectible to a source of water or other treating fluid for permitting injection of fluid into the main tube. The inlet tube is considerably smaller in diameter than the main tube and is disposed at an obtuse angle to the discharge end of the main tube. This orientation of the inlet tube causes the incoming fluid to flow in a current towards the discharge end of the main tube when the lavaging machine is in operation. Thus, fluidized waste material discharged from the patient flows with, rather than against, the current in the speculum. As a result, the painful feeling of pressure on the intestines which a patient normally feels is considerably alleviated.

The speculum is provided in combination with an obturator, which facilitates insertion of the device into the patient's rectal canal and lower intestine. In addition, in order to keep the speculum steady while the obturator is removed and a waste removal hose is attached to the discharge end of the main tube, the speculum is provided with a thumb rest. The thumb rest comprises a flange which extends radially from the outer surface of the main tube approximately diametrically opposite the point of intersection between the main tube and the inlet tube. When removing the obturator from the speculum and attaching the waste removal hose, the technician or physician grasps the speculum between his or her thumb and index finger, allowing the distal side of the thumb rest to press against the back of his or her thumb. Thus, the steadying force exerted by the techician's hand counteracts any forces exerted when the obturator is removed and the waste removal hose is attached. This prevents the speculum from rocking or otherwise moving in the patient's rectal canal and conseqently decreases the patient's pain and discomfort, as well as the possibility of damage to the patient's lower intestinal tract.

Accordingly, it is an object of this invention to provide a new and improved rectal speculum which is simply and inexpensively manufactured and readily disposable.

Another object of the invention is to provide a rectal speculum having a reduced number of parts, making it easy to clean.

Another object of the invention is to provide a rectal speculum with an inlet tube arranged at an obtuse angle with respect to the discharge end of the main tube, in order to produce an inlet current in the discharge direction.

Still another object of the invention is to provide the combination of a rectal speculum and an obturator with means for steadying the speculum while the obturator is being removed.

The foregoing and other objects of the present invention, as well as the invention itself, may be more fully understood from the following description when read in conjunction with the accompanying drawings.

DESCRIPTION OF THE PREFERRED EMBODIMENT

Figure 1:
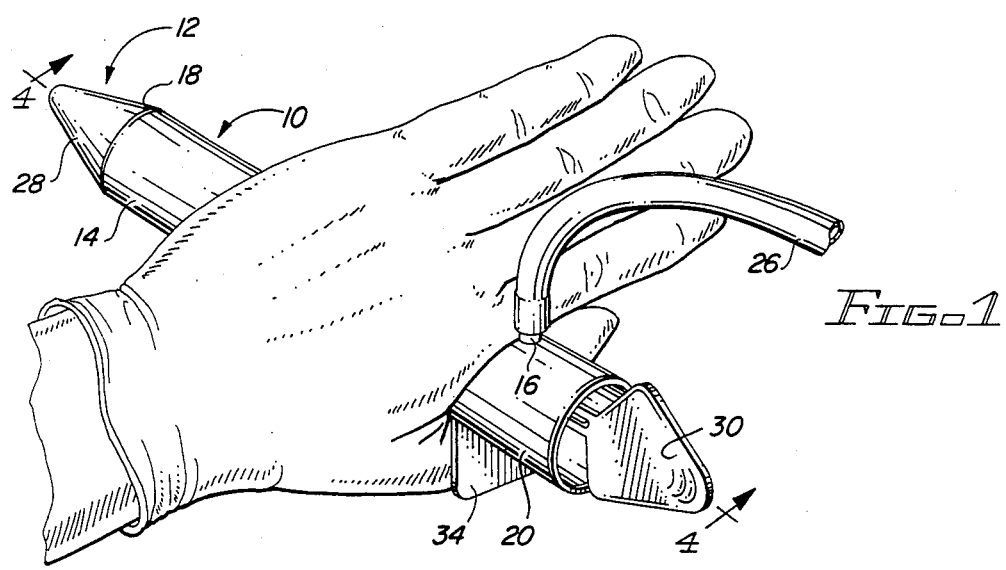
FIG. 1 is a perspective view of the rectal speculum and obturator combination of the present invention being held by a technician or physician.
Figure 2:
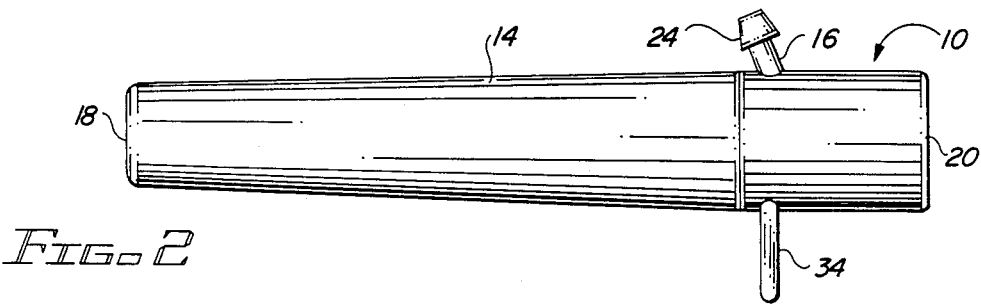
FIG. 2 is an elevation of the rectal speculum of the present invention.
Figure 3:
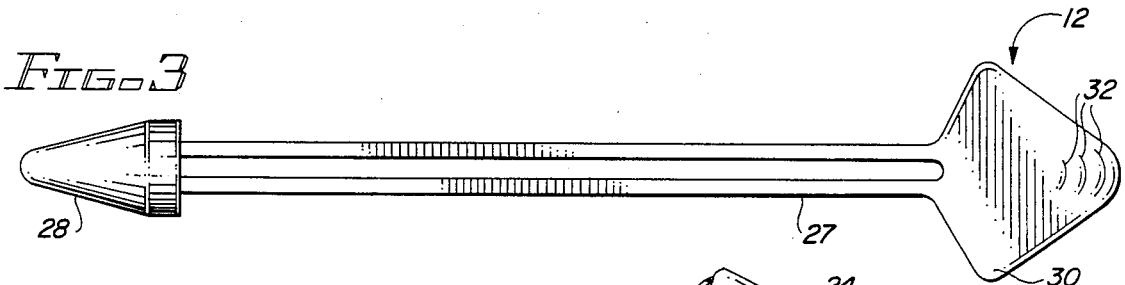
FIG. 3 is an elevation of the obturator of the present invention.
Figure 4:
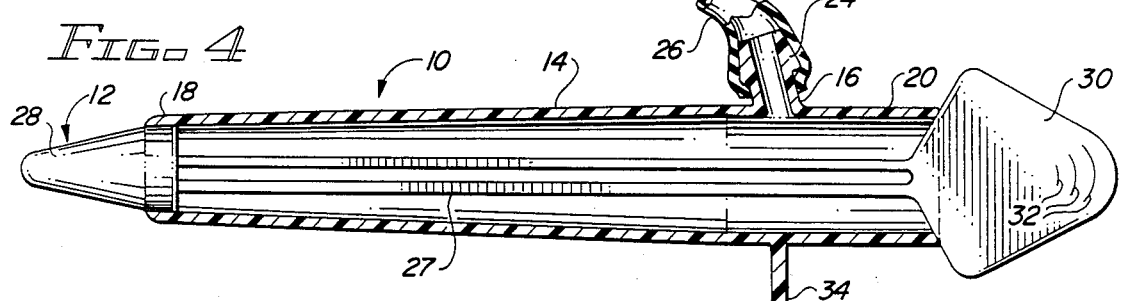
FIG. 4 is a sectional view taken along the line 4—4 of FIG. 1 through the speculum and obturator of the present invention.

Referring more particularly to the drawings, FIG. 1 shows the combination of a speculum 10 and an obturator 12 according to the present invention. The combination is being held between the thumb and index finger of a technician or physician in a manner which allows the obturator 12 to be easily removed e.g. axially withdrawn from the speculum 10 without causing uncomfortable rocking or other movement in a patient's rectum (not shown).

Figure 5:
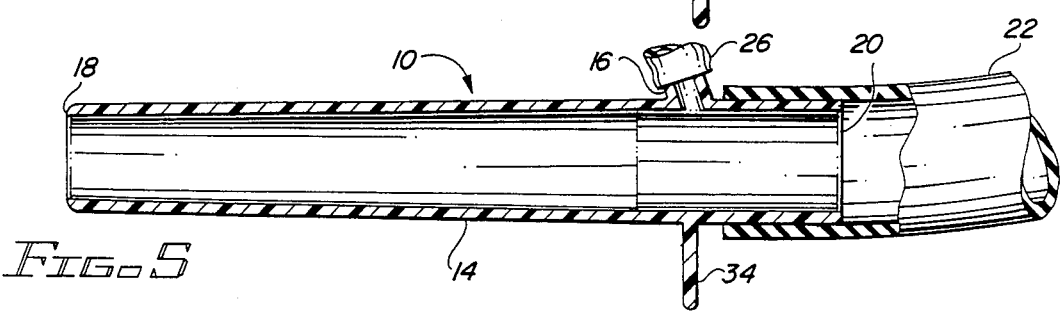
FIG. 5 is a longitudinal section similar to FIG. 4 to show the speculum after the obturator has been removed and a waste removal hose has been connected.

The speculum 10 comprises a pair of intersecting tubes, including an unobstructed main tube 14 and a smaller diameter inlet tube 16 for injecting water or other treatment fluid into the main tube. The main tube 14 includes a distal end 18 adapted for insertion in a patient's rectum (not shown) and a proximal or discharge end 20 adapted for connection to a waste discharge hose 22, as shown in FIG. 5. Preferably, proximal end 20 of the main tube 14 is cylindrical and has an outer diameter slightly greater than the inner diameter of waste discharge hose 22 so as to form a press fit therein. The remaining portion of main tube 14 is preferably slightly tapered toward distal end 18 to facilitate insertion in the rectal canal, with distal end 18 being somewhat rounded for reasons of comfort and safety.

Inlet tube 16 is located proximate the proximal end 20 of the main tube 14, and is disposed to form an obtuse angle with respect to the longitudinal axis of the main tube 14 so that any fluid injected through inlet tube 16 is initially directed away from the distal end 18 of the main tube. This causes a slight current in the discharge direction, which facilitates to removal of fluidized waste matter from the patient's colon when the colonic lavage machine (not shown) is in operation. Preferably, inlet tube 16 terminates in an annular bead 24 forming a fitting for receiving an inlet tubing or hose 26 connected to a source of treated fluids (not shown) in the lavage machine.

The obturator 12 used in combination with the speculum 10 comprises an elongated rod 27 having a tapered, round exterior portion 28 at the distal end, and a handle portion 30 at the proximal end. Normally, the obturator is inserted from the proximal end of main tube 14 of the speculum 10 through the hollow interior to extend through the distal end 18 thereof in order to facilitate insertion of the speculum into the patient's rectum. Once the speculum 10 has been properly positioned, the obturator 12 is then removed from the speculum 10 by use of the handle 30. The handle 30 may be provided with a plurality of ridges 32 in order to facilitate grasping and removal from the speculum.

In addition, in order to prevent rocking or other unnecessary, painful movement of the speculum 10 within the patients rectum while the discharge end of the main tube 14 is being handled as in, for instance, during removal of the obturator 12 and during attachment of the waste removal hose 22, a thumb rest 34 is provided on the main tube 14 of the speculum 10. The thumb rest 34 comprises a flange which extends from the outer surface of the main tube 14 approximately diametrically opposite the point of intersection between the main tube 14 and the inlet tube 16. This structure ensures that when the speculum 10 is held in the position illustrated in FIG. 1, that is, with the back of the technician's thumb resting against the distal side of the thumb rest 34, the knuckle of the index finger bearing against the inlet tube 16 and the palm of the hand resting on the patients posterior, the obturator 12 can be removed and a waste removal hose 22 attached to the proximal end of the speculum without causing the patient any extra discomfort or pain, since the steadying force exerted by the technician's hand will counteract most of the undesirable forces exerted on the main tube 14 during handling.

The speculum 10 and the obturator 12 are preferably both constructed from an inexpensive, light weight material such as polypropylene or other synthetic resins in order to permit disposal after a single use. However, a reusable, easily cleaned version of the speculum and obturator could also be made from a material such as stainless steel or other suitable metals.

While the principles of the invention have now been made clear in the illustrated embodiments, there will be immediately obvious to those skilled in the art, many modifications of structure, arrangements, proportions, the elements, materials and components used in the practice of the invention and otherwise, which are particularly adapted for specific environments and operation requirements without departing from those principles. The appended claims are therefore intended to cover and embrace any such modifications within the limits only of the true spirit and scope of the invention.

I claim as my invention:

1. A rectal speculum for use with a colonic lavage machine, said speculum comprising:

an unobstructed main tube, said main tube including a distal end for insertion into a patient's rectum and a proximal end for connection to a waste discharge hose; and a inlet tube for directing fluids into said main tube, said inlet tube having a diameter less than the diameter of said main tube, and intersecting said main tube at an obtuse angle with respect to the proximal end of said main tube so as to direct fluids away from said distal end of said main tube.

2. The rectal speculum of claim 1, in which said proximal end of said main tube is cylindrical.

3. The rectal speculum of claim 2, in which said inlet tube intersects said main tube on the cylindrical proximal end of said main tube.

4. The rectal speculum of claim 2, in which a portion of said main tube is tapered toward said distal end.

5. The rectal speculum of claim 4, in which said distal end of said main tube is slightly rounded.

6. The rectal speculum of claim 1, further comprising thumb rest means extending radially from the surface of said main tube diametrically opposite the intersection of said main tube with said inlet tube.

7. The rectal speculum of claim 1, in which said speculum is constructed from polypropylene.

8. A rectal speculum assembly for use with a colonic lavage machine, said assembly comprising:
(a) a rectal speculum, said speculum including;
   I. an unobstructed main tube, said main tube having a distal and for insertion into a patient's rectum and a proximal end for connection to a waste discharge hose, and
   II. an inlet tube for directing fluids into said main tube, said inlet tube having a diameter less than the diameter of the main tube, and intersecting said main tube at an obtuse angle with respect to the proximal end of said main tube so as to direct fluids away from said distal end of said main tubes and
(b) an obturator removably positioned in said main tube of said speculum for facilitating insertion of said speculum in a patient's rectum, said obturator including;
   I. an elongated rod extending through said main tube.
   II. a tapered, round exterior portion formed at the distal end of said rod for extending through the distal end of said main tube, and
   III. a handle portion formed at the proximal end of said rod for extending through the proximal end of said main tube to facilitate removal of said obturator from said speculum.

9. The speculum assembly of claim 8, further comprising means for steadying said speculum in a patient's rectum during handling of said proximal end of said main tube.

10. The speculum assembly of claim 9, in which said means for steadying comprises thumb rest means located on said main tube.

11. The speculum assembly of claim 10, in which said thumb rest means comprises a flange extending radially outwardly from the surface of said main tube.

12. The speculum assembly of claim 11, in which said flange is located approximately diametrically opposite the intersection of said main tube and said inlet tube.

13. A rectal speculum assembly for use with a colonic lavage machine, said assembly comprising:
(a) a rectal speculum, said speculum including:
   I. a main tube, said main tube having a distal end for insertion into a patient's rectum, and a proximal end for connection to a waste removal hose, and
   II. an inlet tube intersecting said main tube for directing fluids into said main tube;
(b) an obturator removably positioned in said main tube of said speculum for facilitating insertion of said speculum in a patient's rectum, said obturator including;
   I. an elongated rod extending through said main tube.
   II. a tapered, round exterior portion formed at the distal end of said rod for extending through the distal end of said main tube, and
   III. a handle portion formed at the proximal end of said main tube to facilitate removal of said obturator from said speculum; and
(c) means for steadying said speculum in a patient's rectum during handling of said proximal end of said main tube.

14. The speculum assembly of claim 13, in which said inlet tube is disposed at an obtuse angle relative to said proximal end of said main tube so as to direct fluids away from said distal end of said main tube.

15. The speculum assembly of claim 14, in which said inlet tube comprises means for attachment to a fluid inlet tubing connected to a treatment fluid source in a colonic lavage machine.

16. The speculum assembly of claim 15, in which said means for attachment comprises an annular bead around said inlet tube forming or fitting for receiving said fluid inlet tubing.

17. The speculum assembly of claim 13, in which said means for steadying comprises thumb rest means located on the proximal end of the main tube of said speculum.

18. The speculum assembly of claim 17, in which said thumb rest means comprises a flange extending radially outwardly from the surface of said main tube.

19. The speculum assembly of claim 13, in which said speculum and said obturator are constructed from polypropylene 20. The speculum assembly of claim 13, in which said handle portion of said obturator comprises a plurality of ridges for facilitating grasping of said handle and removal of said obturator from said speculum.

* * * * *